United States Patent [19]
Celoni et al.

[11] Patent Number: 5,624,159
[45] Date of Patent: *Apr. 29, 1997

[54] ADAPTIVE SEATING DEVICE FOR DIAGNOSTIC TESTING

[75] Inventors: Michael J. Celoni, Glendale; Judith L. Kulpa; Michael F. Conmy, both of Milwaukee, all of Wis.

[73] Assignee: Vess Chairs, Inc., Wauwatosa, Wis.

[*] Notice: The portion of the term of this patent subsequent to Oct. 5, 2010, has been disclaimed.

[21] Appl. No.: 64,459

[22] Filed: May 11, 1993

[51] Int. Cl.⁶ .................................................. A47C 1/02
[52] U.S. Cl. .................. 297/325; 297/317; 297/DIG. 10
[58] Field of Search ........................... 297/325, 328, 297/302, 317, DIG. 10

[56] References Cited

U.S. PATENT DOCUMENTS

| | | | |
|---|---|---|---|
| 2,874,689 | 2/1959 | Gavelek | 601/90 |
| 3,299,886 | 1/1967 | Mikan | 297/337 |
| 4,505,514 | 3/1985 | Stockl et al. | 297/322 |
| 4,993,777 | 2/1991 | LaPointe | 297/DIG. 10 |
| 5,061,010 | 10/1991 | LaPointe | 297/DIG. 10 |
| 5,108,202 | 4/1992 | Smith | 297/DIG. 10 |
| 5,215,351 | 6/1993 | LaPointe | 297/DIG. 10 |
| 5,249,838 | 10/1993 | Kulpa et al. | 297/328 |
| 5,294,179 | 3/1994 | Rudes et al. | 297/325 |

FOREIGN PATENT DOCUMENTS 2057980  6/1971  Germany ........................ 297/325

*Primary Examiner*—John T. Kwon
*Attorney, Agent, or Firm*—Ryan, Kees & Hohenfeldt

[57] ABSTRACT

A narrow seating device or chair including a support caddy having lockable ground engaging caster wheels and a seat portion for a patient undergoing a medical test. The seat portion is mounted on the support caddy and tiltable to a plurality of tilt positions. The seat portion has a convexly curved surface which rests on spaced apart rollers on the upper side of the support caddy to enable tilting. A linear actuator having a first end attached to the support caddy and a second end connected to the seat portion provides for tiltable movement of the seat relative to the support.

9 Claims, 2 Drawing Sheets

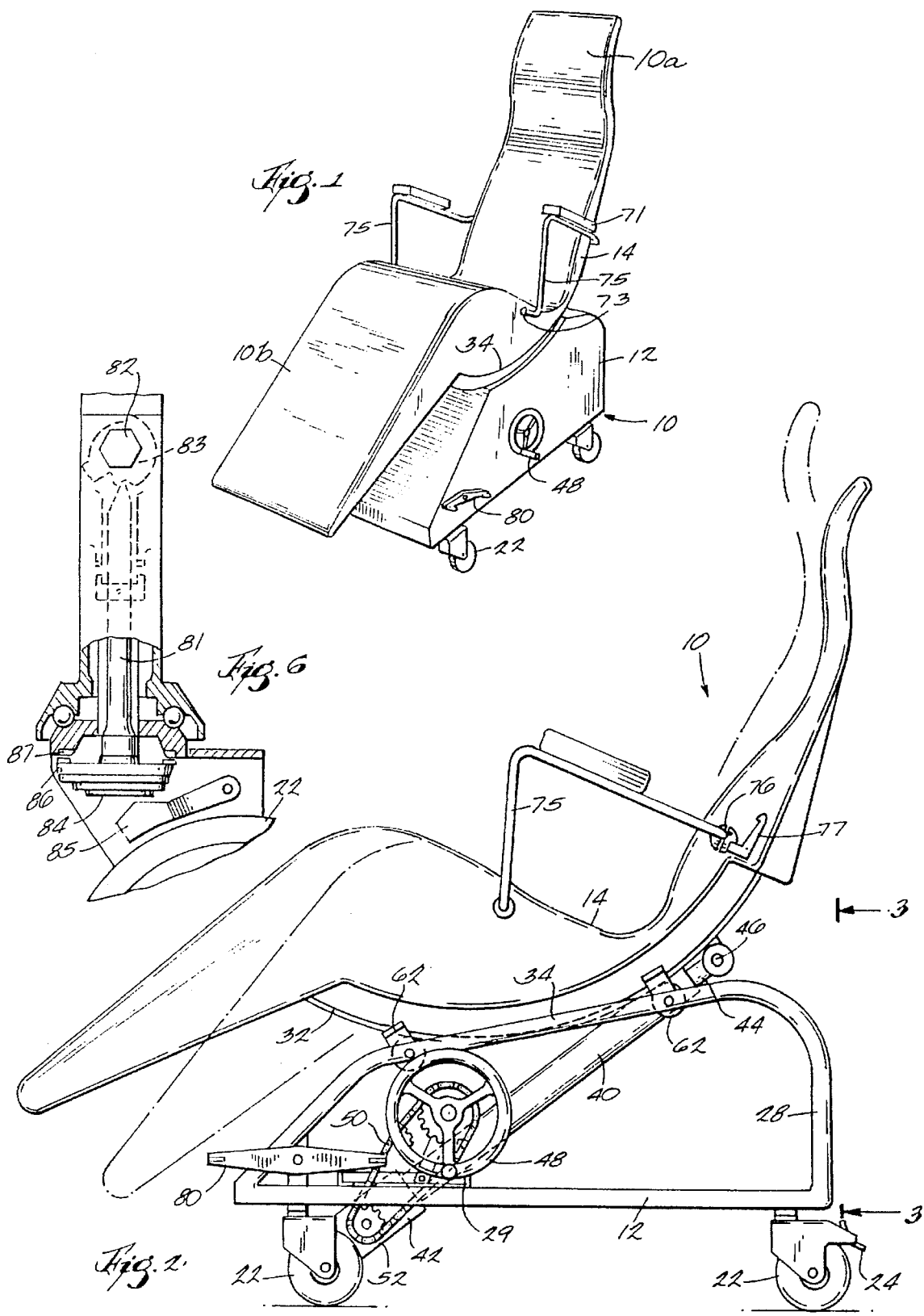

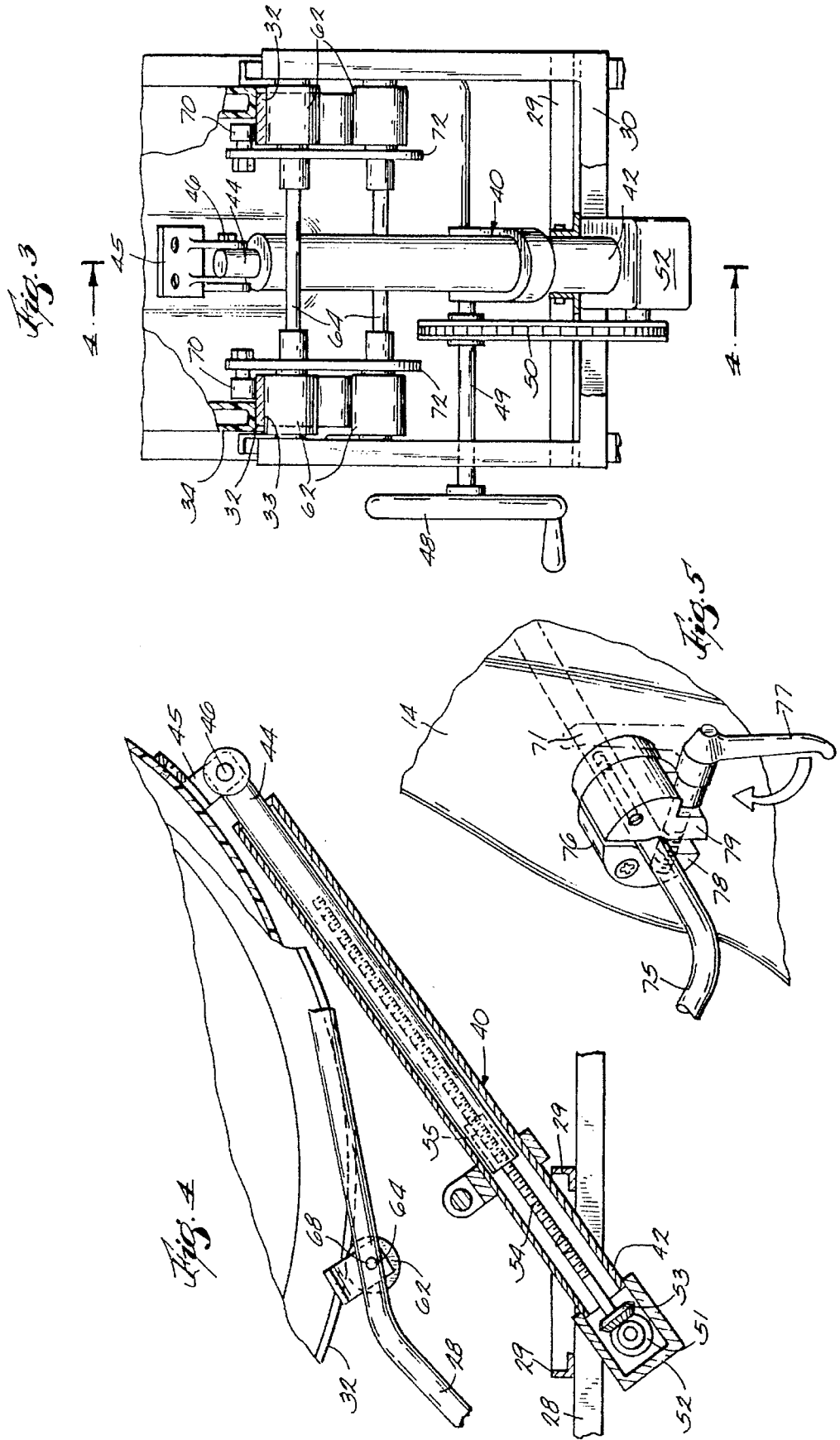

ADAPTIVE SEATING DEVICE FOR DIAGNOSTIC TESTING

BACKGROUND OF THE INVENTION

This invention relates generally to an adaptive seating device (hereinafter called "chair") such as for a patient undergoing a modified barium swallowing fluoroscopic imaging study, and in particular to the construction of the chair which is used to properly position the patient during the. study to optimize the study results. This invention represents a modification and improvement of the chair described in copending application Ser. No. 586,625 filed Sep. 30, 1990.

In the fields of medicine and speech pathology it is sometimes necessary to evaluate and treat persons with dysphagia, a swallowing disorder which interferes with ingestion of food and liquids. Patients can include the neurologically impaired (CVA, ALS, cerebral palsy, myasthenia gravis), orthopedically impaired (Kyphosis, arthritis), cognitively impaired (closed head injury, dementia), and head and neck cancer patients. Typically, the action of the patient's oral cavity, pharynx and esophagus is observed by means of a fluoroscope while the patient swallows a liquid, paste or masticated material, containing barium.

To optimize the result of the study, it is necessary to place the patient in proper position while the radiologic procedure is carried out. In a modified barium swallow study (as contrasted with a simple barium swallow study) the patient must be upright during the study, that is, in a normal physiological position naturally assumed during normal eating and drinking. Patients with the above disorders can exhibit concomitant movement alterations. e.g. paralysis, thereby necessitating seating and positioning adaptations during the study to assure that the patient is placed in a proper position and can remain comfortably and safely in that position. Prior art imaging tables and radiologic equipment do not always accommodate the special positioning needs of some patients.

In the above noted copending application a chair was disclosed in which the seat is supported on the caddy support by means of rotatable members, such as rollers, which are rotatably mounted on the support caddy and engage the underside of a convexly curved portion or member affixed to the underside of the seat. These rollers enable the seat to be tiltably moved fore and aft or positioned to a plurality of tilt positions relative to the support caddy. A flexible metal cable which has its ends secured to the support caddy through a helical tension spring and a turn-buckle releasably secures the seat to the support caddy. The cable is reeved around a pulley which is mounted on the underside of the seat. Releasable locking pins are provided to lock the seat in a desired tilt position to which it has been moved. The present invention represents an improvement over the chair shown in said application.

SUMMARY OF THE INVENTION

A chair in accordance with the present invention generally comprises a support caddy having lockable casters enabling it to be moved across a floor. A seat is further included for accommodating a patient, which seat is tiltably positionable to desired positions on the support caddy by means of an improved tilting system using a linear actuator. The seat is secured in a desired position by means of the actuator, which is preferably manually operated using a hand crank. The seat has a frame with an ergonomically-shaped profile to conveniently and safely seat the patient, and is provided with detachable arm rests.

A chair in accordance with the present invention provides several important advantages over the prior art. It is relatively narrow and is able to fit, with the patient, between a fluoroscopy table and an imaging screen, to facilitate both lateral and anterior/posterior views of the human swallowing tract. It is fabricated of radiolucent materials where appropriate. Its ergonomic shape enables it to accommodate contracted or mobility-impaired patients. The tilting function of the seat enables proper positioning of the patient relative to both the normal upright position of a patient and to the radiologic equipment. Its design facilitates placement in and removal of the patient at bedside and enables convenient and safe transport of the patient to the radiologic facility. It is safe to use for both patient and clinical staff. It is easy to clean and is easy to assemble and disassemble for cleaning, maintenance or storage. It is relatively economical to manufacture.

Other objects and advantages of the invention will become apparent hereinafter.

DESCRIPTION OF THE DRAWING

FIG. 1 is a perspective view of a chair in accordance with the invention taken from the left front side thereof;

FIG. 2 is a left side elevational view of the chair showing the seat in an alternate tilt position in phantom lines;

FIG. 3 is a fragmentary rear view taken along line 3—3 of FIG. 2;

FIG. 4 is a fragmentary cross-sectional view of a portion of the chair taken generally along line 4—4 of FIG. 3;

FIG. 5 is a fragmentary perspective view of a portion of the chair taken showing the arm rest connection; and, FIG. 6 is a fragmentary cross-sectional view of a front wheel locking mechanism used in conjunction with the invention.

DESCRIPTION OF THE PREFERRED EMBODIMENT

Referring to FIGS. 1 and 2, there is shown a chair 10 in accordance with the invention having a head end 10a and a foot end 10b, and which comprises a support caddy 12 and a seat portion 14.

The support caddy 12 comprises a tubular caddy frame 28, including two cross bars 30, on which a caddy housing 26 (not shown) is rigidly mounted. The frame 28 and cross bars 30 are preferably made of metal, such as aluminum, while the housing 26 is preferably formed of plastic, such as polyethylene. The support caddy 12 is provided with four casters 22, each of which has a wheel which can rotate and swivel, and the rear pair of which are provided with a foot operated caster locking lever 24 to lock the caster 22 against rolling and swiveling. The front wheels are provided with a mechanism (FIG. 6) that provides for locking the wheels is a parallel orientation wherein they can rotate but not swivel, or in a fully locked position wherein they will neither rotate nor swivel. The seat portion 14, which can be molded of polyethylene or other plastic material, is covered during use with a seat cushion (not shown) which is preferably molded polyethylene covered for easy cleaning and disinfecting. The seat cushion is described in the above mentioned copending application. The seat portion 14 has an ergonomic shape which, when tilted in upright position, generally places a patient in a normal seated position. The seat portion 14 has an arcuately curved underside 34. The left side edge of curved underside 34 has a correspondingly curved metal rim plate 32 rigidly secured thereto, as FIGS. 1 through 4 show.

The seat portion 14 is tiltably supported on support caddy 12 by means of a plurality of rollers 62, four in the embodiment shown. In this embodiment two spaced roller shafts 64 are provided which have their opposite ends journaled for rotation in shaft axle holes 68 in caddy frame 28. The rollers 62 engage the curved rim plates 32 on opposite sides of seat portion 14. Rollers 70 engage the tops of rim plates 32 as seen in FIG. 3 and prevent chair seat portion 14 from lifted off of caddy 12. Rollers 70 are supported on plates 72 which also prevent seat portion 14 from shifting laterally. The rollers 62 enable the seat portion 14 to be tiltably moved fore and aft to any desired tilt position.

As FIG. 3 shows rim plate 32 is rigidly secured to curved seat underside 34 by screws 33. The rim plate 32, preferably of metal such as plated steel or aluminum, has a free edge extending toward the central axis of the chair. As noted above, roller 70 rides along the top of the rim plate and retains the seat portion 14 on the support caddy 12.

The chair 10 is provided with several optionally usable accessories including two detachable arm rests 75, detachable pillows, leg, waist, torso and head straps (not shown), and various brackets and mounting holes (not shown) on the sides of support caddy 12 to which equipment (not shown) such as IV standards, oxygen bottles and the like, can be securely mounted.

The arm rests 75 are slidably insertable laterally in holes 71 and 73, respectively, in the opposite sides of seat portion 14 as shown. A two piece, pivoting clamp 76 operable by crank 77 is provided for ease of inserting and removing the arm rest 75 as needed. Arm rests 75 also can be positioned inwardly or outwardly to accommodate patients of different sizes. Clamp 76 includes two halves 78 and 79. Pivoted half 78 is pivotable toward or away from stationary half 79 by rotation of crank 77.

The tilting of upper seat portion 14 of chair 10 on base 12 is controlled by a linear actuator 40. The lower end of linear actuator 42 is attached as best seen in FIG. 3 to cross frame members 29 that are integral with lower frame 28. The upper end 44 of linear actuator 40 is pivotally attached to a bracket 45 that is rigidly connected to rim plate 32 by means of a pin 46.

Linear actuator 40 is extended and retracted by means of a hand crank 48. Crank 48 is connected by means of a shaft 49 and chain 50 to a bevel gear 51 located within a gear box 52. Bevel gear 51 meshes with a bevel gear 53 on the end of threaded shaft 54 located within lower end 42 of the linear actuator 40. Threaded end 54 is engaged with threads 55 that are integral with upper end 44 of actuator 40. Thus, rotation of crank 48 will raise or lower seat 14 as required for a particular patient.

The locking mechanism for the front wheels is shown in FIG. 6. Such mechanisms are commercially available as a Tente® Model 2474 Swivel. The wheels have three positions. In the central position illustrated in FIG. 6, wheel 22 is free to rotate and to swivel. In the neutral position a hexagonal shaft 82, which is rigidly connected to handles 80 is in a position wherein cam 83 allows pin 81 to be in an intermediate location. Rotation of shaft 82 clockwise in FIG. 6 causes shaft 81 to be extended. In the extended position, lower end 84 of shaft 81 forces a brake 85 into contact with wheel 22. In this position, the wheel can neither rotate nor swivel. On the other hand, rotation of shaft 82 counterclockwise from the position shown in FIG. 6 allows shaft 81 to be retracted. In the retracted position lugs 86 engage slots 87 so that the wheels will only face in a forward-rearward orientation from which they cannot swivel unless lever 80 is once again rotated clockwise. Such locking of wheels 22 against swiveling facilitates transportation of the chair, for example, in hallways and corridors. Shaft 81 is upwardly biased so that the same will remain fully engaged against cam 83.

Operation

The seat portion 14 can be tilted to and locked in a normal seating position to receive an ambulatory patient or can be moved alongside and parallel to a bed (not shown) and tilted to a reclined position to receive a recumbent patient who is transferred from bed to chair 10 in accordance with conventional hospital practice. In either case, the casters 22 are locked to immobilize chair 10 as the patient occupies or is transferred to chair 10. Straps are then emplaced, as required, to safely secure the patient in chair 10, and arm rest 75 may be emplaced. Various optional equipment required by the patient, such as IV standards, oxygen bottles and the like, may be attached to chair 10. When the patient is ready, the casters 22 are unlocked and the chair 10 is rolled to the site of the radiological equipment (not shown) and chair 10 is properly positioned in the narrow space between components of the fluoroscopic equipment. The arm rest 75 may be adjusted or removed, as required. The tilt of seat portion 14 is adjusted, as required, by means of crank 48, and the casters 22 are locked. After the fluoroscopic examination is completed, the chair 10 is withdrawn from the narrow space and the chair, with patient therein, is transported to the appropriate place whereat the patient is assisted in leaving chair 10.

An actual embodiment of the chair 10 was on the order of 15½" wide, 50" high, 52" long and weighed 135 pounds. The chair 10 tapered to 13" at the uppermost head end of the seat portion 14 to facilitate fitting between closely placed components of the radiological equipment.

While the apparatus hereinbefore described is effectively adapted to fulfill the aforesaid objects, it is to be understood that the invention is not intended to be limited to the specific preferred embodiment of adaptive seating device set forth above. Rather, it is to be taken as including all reasonable equivalents within the scope of the following claims.

We claim:

1. An adaptive seating device comprising:
   a support;
   a seat portion for accommodating a person mounted on and tiltably positionable on said support,
   said seat portion having an arcuately curved surface on its underside;
   rotatable means mounted on said support and engaged with said curved surface on said seat portion to support said seat portion and to enable said seat portion to be tiltably moved by rolling movement of said arcuately curved surface on said rotatable means to any one of a plurality of tilt positions relative to said support; and
   a linear actuator having first and second ends, said first end being attached to said support and said second end being connected to said seat portion to whereby said seat portion is tiltably movable relative to said support.

2. A device according to claim 1 wherein said rotatable means comprises spaced apart rollers, each roller having an axis of rotation spaced apart from and parallel to the axis of rotation of the other roller.

3. A device according to claim 1 wherein said linear actuator is manually extendable and retractable by means of a hand crank.

4. A device according to claim 3 wherein said linear actuator is extended and retracted by rotation of a hand crank that rotates a bevel gear that is intermeshed with a gear connected to said actuator, rotation of which lengthens and shortens said actuator.

5. A device according to claim 4 wherein said support means is provided with ground engaging wheels.

6. A device according to claim 5 including detachable arm rest means for said seat portion.

7. An adaptive seating device for a patient undergoing a modified barium swallow study comprising:

a. a support caddy having releasably lockable ground engaging caster wheels and a pair of spaced apart rollers near the upper side thereof;

b. a seat portion which is mounted on said support caddy and tiltable to any one of a plurality of tilt positions relative to said support caddy, said seat portion having a convex downwardly facing curved surface at its underside which rests on said spaced apart rollers to enable tilting of said seat portion by rolling movement of said curved surface on said rollers, said curved surface being provided with metal rims on each side thereof, said rims having edges projecting toward the centerline of said seat portion;

c. a pair of rollers engaging the top surfaces of said metal rims and securing said seat portion to said support caddy while allowing for tilting of said seat portion, d. a linear actuator having first and second ends, said first end being attached to said support caddy and said second end being connected to said seat portion to whereby said seat portion is tiltably movable relative to said support caddy.

8. A device according to claim 7 further including at least one arm rest detachably mounted on a side of said device.

9. A device according to claim 7 further wherein the front wheels are provided with means to releasably lock them in a parallel, non-swiveling position.

* * * * *